United States Patent
Persson et al.

(10) Patent No.: US 9,561,382 B2
(45) Date of Patent: Feb. 7, 2017

(54) SYSTEM AND METHOD FOR LOW POWER COMMUNICATION BETWEEN IMPLANTABLE DEVICES

(71) Applicant: Pacesetter, Inc., Sunnyvale, CA (US)

(72) Inventors: Benjamin T. Persson, Sunnyvale, CA (US); Gleb Klimovitch, Santa Clara, CA (US); Kenneth J. Carroll, Los Altos, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/931,736

(22) Filed: Nov. 3, 2015

(65) Prior Publication Data

US 2016/0121129 A1    May 5, 2016

Related U.S. Application Data

(60) Provisional application No. 62/084,476, filed on Nov. 25, 2014, provisional application No. 62/074,541, filed on Nov. 3, 2014.

(51) Int. Cl.

| | |
|---|---|
| *A61N 1/372* | (2006.01) |
| *A61N 1/37* | (2006.01) |
| *A61N 1/375* | (2006.01) |
| *A61N 1/362* | (2006.01) |
| *H04W 56/00* | (2009.01) |
| *A61N 1/365* | (2006.01) |
| *H04W 52/04* | (2009.01) |

(52) U.S. Cl.
CPC ......... *A61N 1/37288* (2013.01); *A61N 1/3622* (2013.01); *A61N 1/3756* (2013.01); *A61N 1/37235* (2013.01); *H04W 56/001* (2013.01); *A61N 1/36514* (2013.01); *A61N 1/3702* (2013.01); *A61N 1/37217* (2013.01); *H04W 52/04* (2013.01)

(58) Field of Classification Search
None
See application file for complete search history.

(56) References Cited

U.S. PATENT DOCUMENTS

| | | | |
|---|---|---|---|
| 7,162,307 B2* | 1/2007 | Patrias | A61N 1/37252 128/903 |
| 7,991,467 B2* | 8/2011 | Markowitz | A61N 1/025 607/14 |
| 8,386,049 B2* | 2/2013 | Persson | A61N 1/37276 607/32 |

(Continued)

*Primary Examiner* — Brian T Gedeon
(74) *Attorney, Agent, or Firm* — Theresa A. Raymer

(57) ABSTRACT

In accordance with an embodiment, apparatuses and methods are provided for coordinating operation between leadless pacemakers (LPs) located in different chambers of the heart. A method includes configuring a local LP to receive communications from a remote LP through conductive communication over first and second channels, maintaining the first channel active for at least a portion of a time when the second channel is inactive to listen for event messages from the remote LP, detecting an incoming signal at the local LP over the first channel, determining whether the incoming signal received over the first channel corresponds to an LP wakeup notice, when the incoming signal corresponds to the LP wakeup notice, activating the second channel at the local LP, and receiving an event message over the second channel from the remote LP.

25 Claims, 6 Drawing Sheets

(56) References Cited

U.S. PATENT DOCUMENTS

| | | | | |
|---|---|---|---|---|
| 8,554,333 B2* | 10/2013 | Wu | ............... | A61N 1/37276 340/10.33 |
| 2007/0049992 A1* | 3/2007 | Freeberg | ............ | A61N 1/37211 607/60 |
| 2011/0202103 A1* | 8/2011 | Wikman | ............ | A61N 1/37276 607/25 |
| 2015/0174414 A1* | 6/2015 | Stahmann | ............ | A61N 1/3708 607/4 |

* cited by examiner

SYSTEM AND METHOD FOR LOW POWER COMMUNICATION BETWEEN IMPLANTABLE DEVICES

CROSS REFERENCE TO RELATED APPLICATIONS

This application claims the benefit of U.S. Provisional Application No. 62/084,476, entitled IMPLANTABLE DEVICE INTRA-CARDIAC COMMUNICATIONS SYSTEM AND METHOD, filed Nov. 25, 2014. This application also claims the benefit of U.S. Provisional Application No. 62/074,541, entitled IMPLANTABLE DEVICE INTRA-CARDIAC COMMUNICATIONS SYSTEM AND METHOD, filed Nov. 3, 2014. Each patent application identified above is incorporated herein by reference in its entirety to provide continuity of disclosure.

FIELD OF THE INVENTION

Embodiments herein generally relate to methods and systems for communication between implantable devices.

BACKGROUND OF THE INVENTION

Currently, implantable medical devices (IMDs) utilize one or more electrically-conductive leads (which traverse blood vessels and heart chambers) in order to connect a canister with electronics and a power source (the can) to electrodes affixed to the heart for the purpose of electrically exciting cardiac tissue (pacing) and measuring myocardial electrical activity (sensing). These leads may experience certain limitations, such as incidences of venous stenosis or thrombosis, device-related endocarditis, lead perforation of the tricuspid valve and concomitant tricuspid stenosis; and lacerations of the right atrium, superior vena cava, and innominate vein or pulmonary embolization of electrode fragments during lead extraction. Further, conventional pacemakers with left ventricle (LV) pacing/sensing capability require multiple leads and a complex header on the pacemaker.

A small sized IMD has been proposed that mitigates the aforementioned complications, termed a leadless pacemaker (LP), that is characterized by the following features: electrodes are affixed directly to the "can" of the device; the entire device is attached to or within the heart; and the LP is capable of pacing and sensing in the chamber of the heart where it is implanted.

The LPs that have been proposed thus far offer limited functional capability. The LP is able to sense in one chamber and deliver pacing pulses in that same chamber, and thus offers single chamber functionality. For example, an LP device that is located in the right atrium would be limited to offering AAI mode functionality. An AAI mode LP can only sense in the right atrium, pace in the right atrium and inhibit pacing function when an intrinsic event is detected in the right atrium within a preset time limit. Similarly, an LP device that is located in the right ventricle would be limited to offering VVI mode functionality. A VVI mode LP can only sense in the right ventricle, pace in the right ventricle and inhibit pacing function when an intrinsic event is detected in the right ventricle within a preset time limit.

It has been proposed to implant sets of multiple LP devices within a single patient, such as one or more LP devices located in the right atrium and one or more LP devices located in the right ventricle. The atrial LP devices and the ventricular LP devices wirelessly communicate with one another to convey pacing and sensing information between each other to coordinate pacing and sensing operations between the various LP devices. However, these sets of multiple LP devices experience various limitations.

For conventional implanted devices such as pacemakers, communication, which is normally RF or inductive communication, is relatively infrequent and is limited to device implantation, patient follow-up, and more recently, patient monitoring. In any of these cases, the time between communication sessions is very large relative to the communication time of any given session. This allows the implanted device to periodically check for the presence of the external instrument and since that external instrument has a significantly better power source (not limited by patient anatomy and related safety issues) it can carry more of the communication burden, offloading to the implant only the minimum function necessary to communicate. For example, the external instrument can transmit stronger signals and can apply more signal processing power to the reception and decoding of the received signals.

In the case of intercommunication between implants, e.g., leadless pacemakers that are configured to fit within a chamber of a patient's heart, however, the power sources are heavily constrained due to patient anatomy and related safety issues. In addition, in order for two or more implantable medical devices to deliver coordinated therapy or perform synchronized data collection, information must be regularly exchanged between the devices, e.g., on a pulse by pulse basis. Any excess power consumption needed for inter-device communication will reduce device battery/ power cell longevity, requiring the patient to undergo more frequent operations to have their implants replaced.

Further, communication between an external programmer and an implant, e.g., RF communication, usually permits large transmitter to receiver separations in comparison with the wavelength of communication. Implant to implant communication, on the other hand, may require communication to occur in near-field, i.e., the transmitter to receiver separation may be much smaller than the wavelength of communication, at hundreds of kHz, resulting in a higher noise to signal ratio and requiring higher processing power for decoding the signal.

Additionally, in the case of using conducted communication through the body tissue, the signal is greatly attenuated. Estimates are for a 60 dB to >80 dB attenuation over only a few cm of device separation (with electrode separation of 3 cm). Poor relative orientations can cause even further signal deterioration. A single chamber leadless cardiac pacemaker can receive communication pulses from an external instrument since that instrument can overcome that attenuation with high amplitude pulses. Also the external instrument can tightly control the signal pulse timing to simplify the receiver. If specific messages are lost by distortion or interference, the system can resend the message, with little implication to patient safety.

A dual chamber leadless pacemaker system must overcome the high signal attenuation using lower amplitude (subthreshold) pulses and with limited electrode spacing. There is less control over the electrode orientation so the receiver sensitivity must be much higher to detect and decode low level signals (<1 mV). The signal timing must also be recovered as cardiac events can occur at any time. The communication power budget is more limited and there should be an equal balance between transmitter and receiver complexity as both devices may need to relay information.

There is also a tighter real-time constraint as message information is a part of the active system timing (as compared to reprogramming or diagnostics for an external instrument communication link). The communication link must also be more reliable as the penalty for dropped messages is greater. Due to the tight power constraints, designing a suitable error coding scheme is more challenging since long error codes will consume additional current.

Each of the LP devices must expend significant power to maintain the wireless communications links. The wireless communications links should be maintained in order to constantly convey pacing and sensing information between, for example, atrial LP device(s) and ventricular LP device (s). This pacing and sensing information is necessary to maintain continuous synchronous operation, which in turn draws a large amount of battery/power cell power.

Further, it is difficult to maintain a reliable wireless communications link between LP devices. The LP devices utilize low power transceivers that are located in a constantly changing environment within the associated heart chamber. The transmission characteristics of the environment surrounding the LP device change due in part to the continuous cyclical motion of the heart and change in blood volume. Hence, the potential exists that the communications link is broken or intermittent.

SUMMARY

In accordance with one embodiment, a method is provided for coordinating operation between leadless pacemakers (LPs) located in different chambers of a heart. The method includes configuring a local LP to receive communications from a remote LP through conductive communication over first and second channels, maintaining the first channel active for at least a portion of a time when the second channel is inactive to listen for event messages from the remote LP, detecting an incoming signal at the local LP over the first channel, determining whether the incoming signal received over the first channel corresponds to an LP wakeup notice, when the incoming signal corresponds to the LP wakeup notice, activating the second channel at the local LP, and receiving an event message over the second channel from the remote LP.

In accordance with another embodiment, a method is provided for coordinating operation between first and second leadless pacemakers (LPs) configured to be implanted within first and second chambers of a heart. The method includes transmitting an event marker through conductive communication using electrodes located along a housing of the first LP, the event marker indicative of one of a local paced or sensed event in the first chamber, detecting, the event marker at the second LP, identifying the event marker at the second LP based on a predetermined pattern indicating that an event of interest has occurred in the first chamber, and in response to identifying the event marker, initiating a related action in the second chamber.

In accordance with another embodiment, a leadless pacemaker (LP) for use in a cardiac stimulation system is provided. The LP includes a first receiver configured to receive an LP wakeup notice from a remote LP, a second receiver configured to activate, in response to the first receiver receiving the LP wakeup notice, and receive an event message from the remote LP, the event message including an event marker indicative of at least one a sensed event and a paced event, and a processor coupled to the first and second receiver and configured to decode the event message.

Alternatively, the method further comprises transmitting the LP message trigger pulse(s) or pattern over the first channel from the remote LP and thereafter transmitting the event message over the second channel from the remote LP. The message includes at minimum a unique sync pattern to indicate a valid message. Optionally, in the case of a dual-chamber pacemaker at least two event message patterns will indicate the occurrence of either a paced or sensed event in the remote LP. An optional message extension may be provided to pass additional status or control information as well

BRIEF DESCRIPTION OF THE DRAWINGS

Embodiments of the invention relating to both structure and method of operation may best be understood by referring to the following description and accompanying drawings, in which similar reference characters denote similar elements throughout the several views.

DETAILED DESCRIPTION

In some embodiments of an illustrative cardiac pacing system, one or more leadless cardiac pacemakers with low-power conducted communication can perform single-chamber pacing, dual-chamber pacing, CRT-D, or other pacing, and may or may not be co-implanted with an ICD.

Figure 1:
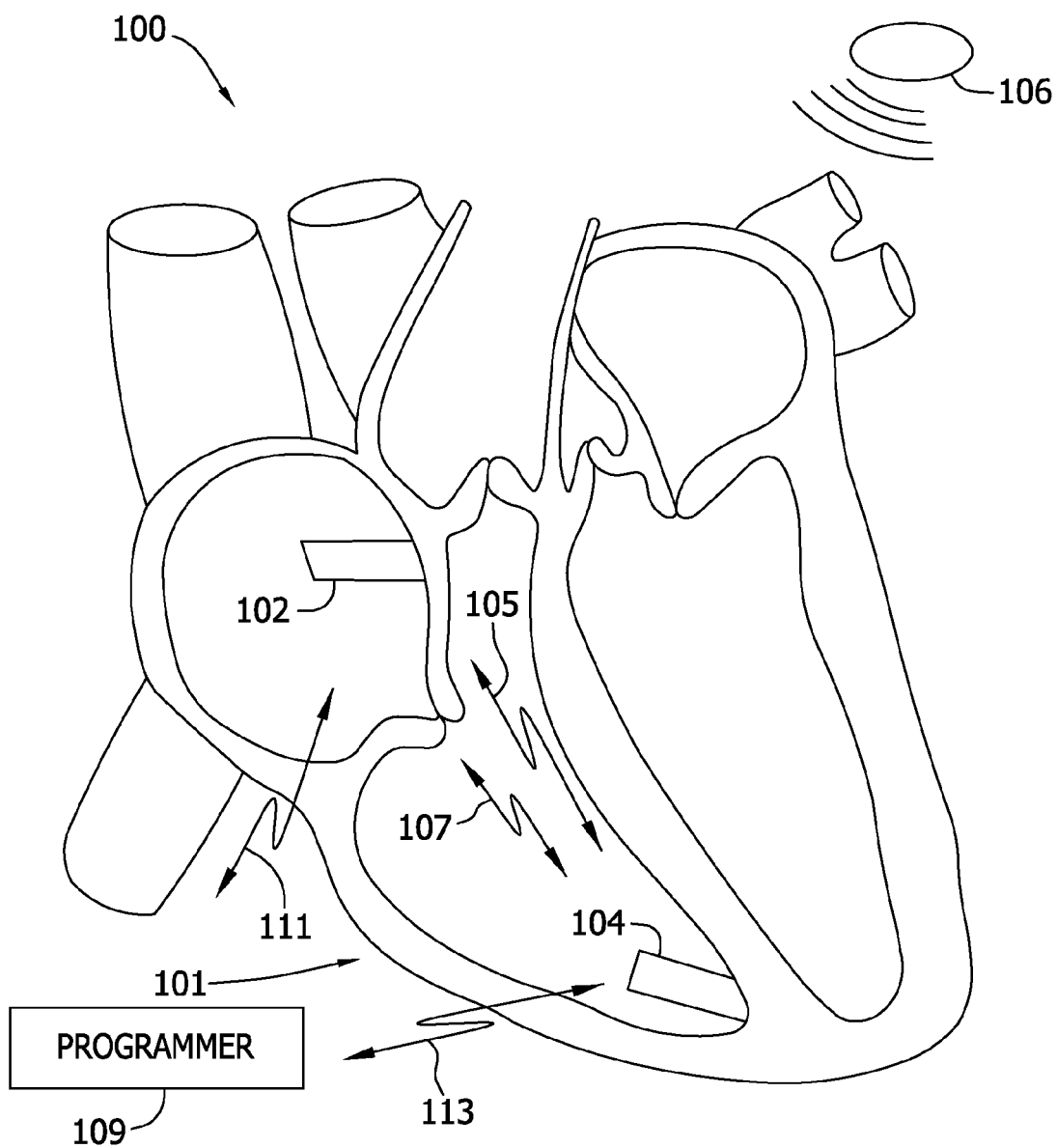
FIG. 1 illustrates a system formed in accordance with embodiments herein as implanted in a heart.
Figure 2:
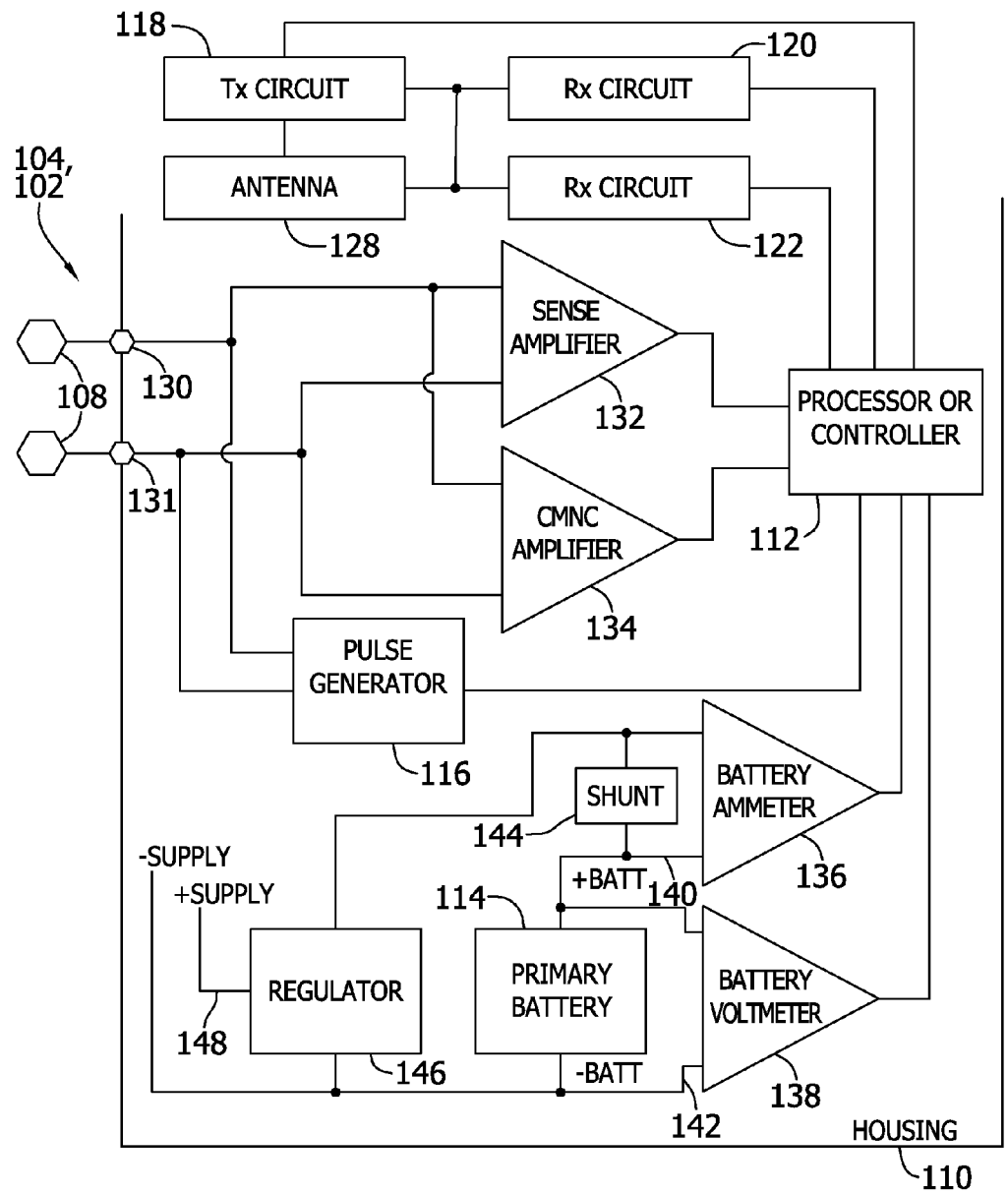
FIG. 2 illustrates a block diagram of a single LP in accordance with embodiments herein.

FIG. 1 illustrates a system 100 formed in accordance with embodiments herein as implanted in a heart 101. The system 100 comprises two or more leadless pacemakers (LPs) 102 and 104 located in different chambers of the heart. FIG. 2 is a pictorial diagram shows an embodiment for portions of the electronics within LP 102, 104 configured to provide conducted communication through the sensing/pacing electrode.

In this embodiment, LP 102 is located in a right atrium, while LP 104 is located in a right ventricle. LPs 102 and 104 communicate with one another to inform one another of various local physiologic activities, such as local intrinsic events, local paced events and the like. LPs 102 and 104 may be constructed in a similar manner, but operate differently based upon which chamber LP 102 or 104 is located. LPs 102 and 104 may utilize two separate and distinct communications channels 105 and 107 that operate as explained herein to reduce power usage between and during implant event messages. In certain embodiments, LPs 102 and 104 may communicate over more than just first and second communications channels 105 and 107. In certain embodiments, LPs 102 and 104 may communicate over one common communication channel 105.

The term "channel" is used in a very broad manner to refer to a logical connection between one or more LPs, IMDs, programmers or other device, over which information is transferred. The channel can be one of several characteristics that either help distinguish the two message types from each other or allow two or more different receivers (or receiver operational modes) to detect the message with lower power consumption and/or increased reliability. The channels may use different spectral frequency bands that may be relatively wideband and may partially overlap. In some embodiments, this may mean using different pulse widths to limit the required receiver bandwidth of one of the receivers (and therefore power). It may also mean different signal amplitudes, modulation schemes, or message error coding as well. For example, as described herein, a low frequency conducted pulse may be used to trigger (e.g., 'wakeup') high frequency message detection, in order to facilitate optimizing total receive and transmit power. In such embodiment, the first 'wakeup' channel could be using conducted communication but the second channel may use another communication technique entirely, such as inductive or RF. Further, in some embodiments, the methods and systems use conductive communication for both channels, due to fewer components, lower cost, and lower power requirements. Thus the term channel is not limited to any particular frequency configurations or physical channels. Instead, a channel is used to convey an information signal from one or several senders (or transmitters) to one or several receivers. Separate channels may be associated with common or different bandwidths. In one example, the channels may be differentiated from one another based on a pulse width of communications messages. One purpose/characteristic of the separate channels is that one of the channels can be defined to have characteristics that allow the channel to be somewhat crudely detected using a low-power always on receiver (coarse detection), while the second channel can be defined to have characteristics that allow confirmation and messaging (with a fine detection receiver).

The communications messages sent utilizing the two channels may or may not utilize a carrier frequency. Using no-carrier communication results in saving significant power that would otherwise be spent on carrier transmission. More specifically, passband communications modulate a carrier frequency in order to place signals in a band that can then be 'selected' (and isolated from other bands) and converted back to baseband. This is very useful for isolating channels, but requires a continuous carrier signal to modulate. For devices with power constraints, however, when transmitting a carrier, the signal amplitude must generally be extremely low (otherwise the power budget will be too high). However, for communication between LPs, low amplitude signal are ineffective, because the signals will be attenuated very strongly by tissue over even short ranges (e.g., an atrial to ventricular distance). Accordingly, using no-carrier communication may be beneficial, even when communicating with a programmer over a longer distance at a higher power transmission. For communication between LPs, in some embodiments, a single pulse (or at most a few pulses) is used to represent a bit, so no carrier signals are used.

In some embodiments, one or more leadless cardiac pacemakers 102 and 104 can be co-implanted with the implantable cardioverter-defibrillator (ICD) 106. In certain embodiments, LPs 102 and 104 communicate with one another, and/or with an ICD 106 by conductive communication through the same electrodes as used for sensing and/or delivery of pacing therapy. When conductive communication is maintained through the same electrodes as used for pacing, the system 100 may omit an antenna or telemetry coil in one or more of LPs 102 and 104.

Each leadless cardiac pacemaker 102, 104 uses two or more electrodes located within, on, or within a few centimeters of the housing of the pacemaker, for pacing and sensing at the cardiac chamber, for bidirectional communication with one another, with an external device, or programmer 109, and with the ICD 106.

In accordance with one embodiment, a method is provided for coordinating operation between leadless pacemakers (LPs) located in different chambers of the heart. The method configures a local LP to receive communications from a remote LP through conductive communication over first and second channels. The method maintains the first channel active for at least a portion of a time when the second channel is inactive to listen for event messages from a remote LP. The method detects an incoming signal at the local LP over the first channel. The method also determines whether the incoming signal received over the first channel corresponds to an LP wakeup notice. When the incoming signal corresponds to the LP wakeup notice, the method activates the second channel at the local LP. The method also receives an event message over the second channel from the remote LP.

The proposed implant communications scheme uses conducted signal transmission similar to that used for a single chamber VVI leadless pacemaker to communicate to a programmer. However, in this case, since the receiving device does not know when to expect an event from the transmitting device it has an 'always-on' detecting receiver that has very low current consumption (<500 nano-amperes (nA)). Because of this low current requirement, it has limited bandwidth and cannot differentiate different messages well enough to decode information but is only used as a detector to indicate that a message is about to be sent. Any message sent by the transmitter will be preceded by a trigger pulse or pulse pattern to alert this receiver. Whenever the detecting receiver observes a trigger pulse or pattern, it will activate the message decoding receiver for a set time period to decode the incoming message. The message decoding receiver has a higher current which is required to get more signal processing bandwidth to decode the higher frequency pulses of the message itself.

Figure 3:
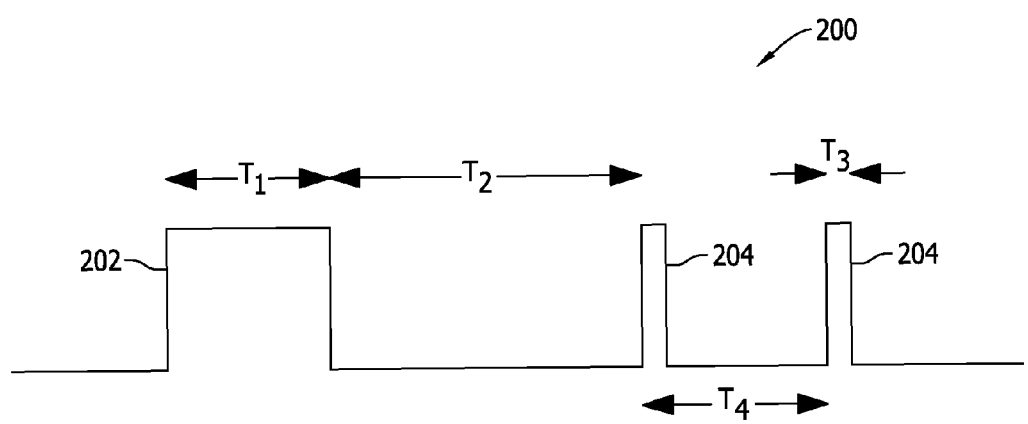
FIG. 3 is a timing diagram illustrating message timing between a message transmitter and a message receiver according to one embodiment.

FIG. 3 is a timing diagram 200 illustrating the most basic version of such message timing between a message transmitter (e.g., LP 102) and a message receiver (e.g., LP 104) according to one embodiment. A wakeup, or trigger pulse 202 has a width, $T_1$, that is optimized to be wide enough such that a low current receiver can detect the expected minimum signal level within the current budget. Specifically, narrower pulse widths impose higher current requirements on the receiver for detection and wider pulse widths require higher transmit current. As an example, a trigger pulse width $T_1$ of 30 microseconds (μs) may require a 300 nA detector in order to detect a received pulse amplitude below 1 mV, and may consume approximately 180 nA to transmit 3 volt (V) pulses into a 500 ohm (Ω) load at 60 beats per minute (bpm).

Accordingly, the receiver uses a detection circuit that can detect these pulses and that has a reasonable current consumption to maintain reasonable device longevity. In such a system, tradeoffs may be made to gain sufficient signal sensitivity by requiring a larger power cell or sacrificing device longevity. Further, in a dual-chamber leadless pacemaker system, it is highly desirable to minimize device size, particularly in the atrium implant. To achieve sufficient device longevity, a total current budget for the implant communication scheme should be kept to a reasonable fraction of the overall device current draw. In such a system, the aim is to apply as much of the battery/power cell capacity to delivering pacing therapy, so the implant communication current budget should be kept under 1 µA if possible. In such a scheme, the largest portion of that budget is targeted for the trigger pulse detection in order to offer the most robust performance under different positions and device orientations. A minimum sensitivity may be between 100 µV and 10 millivolts (mV), and preferably <1 mV. A trigger pulse detection circuit has been demonstrated which delivers this sensitivity with under 500 nA current draw.

One or more message content pulses 204 are transmitted a predetermined interval, $T_2$, after transmission of trigger pulse 202. The predetermined interval $T_2$ allows the message decoding receiver time to activate and stabilize in response to trigger pulse 202. Message content pulses 204 may have a message pulse width, $T_3$, that is much narrower than trigger pulse width $T_1$ to allow more bits to encode the information and allow improved error detection to confirm the information. In contrast, using a relatively wide message pulse width $T_3$ for the information portion of the message would result in a significant transmit current. Per the 3V, 500Ω example, the transmit current during a pulse would be 6 mA. Accordingly, it is desirable to narrow message content pulses 204 and reduce their number. As the pulse widths narrow, the receiver bandwidth and current consumption increases, however, it is still only a fraction of the transmit current.

A typical pacemaker features a high speed clock for the microcontroller which may have a frequency between 100 kilohertz (kHz) and 10 megahertz (MHz), and typically 1 Mhz. With a 1 MHz clock, the design may transmit 1 µs message pulses which results in a 6 nA average transmission current for each 3 V pulse in the message (at a 1 Hz typical pacemaker message rate). A message receiver has been demonstrated that can detect sub-millivolt, 1 µs pulses with a current draw of <60 µA. At this frequency, the receiver current is one hundred times less than the transmitter current during pulse transmission. The message length may be kept short to minimize the receiver current. For example, at the 1 Hz messaging rate, an overall message length under 500 µs will have an average current draw of 30 nA for the messaging receiver. The number of transmitted pulses should also be minimized to reduce the transmission current.

In this embodiment, the receiver performs timing recovery to properly decode the message. In order to avoid transmitting separate pulses for synchronizing and message information, the embodiments described herein combine the most critical message information (in the case of a pacemaker, whether the event is a paced or sensed event) with a synchronization word (a "syncword") needed for timing recovery. In this embodiment, each message begins with a syncword marker. Goals for the syncword coding including i) using "minimal pulses" to reduce transmit current ii) using unique syncwords that do not match any time-shifted version of other syncwords, and iii) selecting syncword pairs so that properties i) and ii) are maintained even with one or more bit-errors. Notably, longer syncwords allow for more bit-error detection and correction.

In this embodiment, the syncword event markers are used to discriminate the two basic event types. However, because the bit timing is also recovered, additional bits may then be sent to extend the message information. For any frequently sent information, short codings may be sent with pulse-position modulation such that the value is encoded by the position of a single pulse within N possible pulse locations.

A relatively simple example is shown in FIG. 3 with the syncword having two narrow message content pulses 204 of width $T_3$ separated by a spacing of $T_4$. For the case of a pacemaker, a communication message may be limited to indication of either pace or sense.

The two messages may simply be distinguished from one another by a difference in pulse separation. For example, the receiver device can use a fast clock (e.g., at nominally 1 MHz) to start a timer to count the interval between pulses to determine which event was transmitted. This scheme has minimal power and complexity however if either of the narrow pulses go undetected the receiver cannot determine which message was sent.

Figure 4:
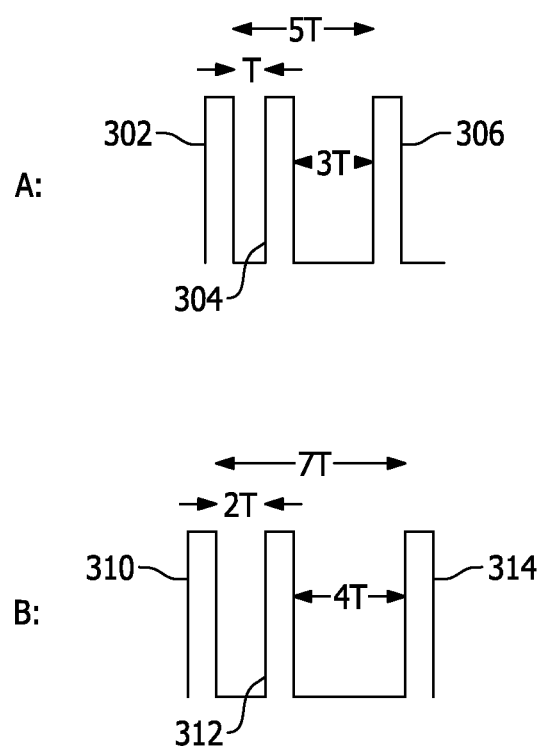
FIG. 4 is a timing diagram illustrating message timing between a message transmitter and a message receiver according to an alternative embodiment.

A more robust scheme allows for bit errors by using more transmitted bits as shown in FIG. 4. By adding a third pulse and using different pulse spacing between consecutive pulses and between non-consecutive pulses (in this case first and last pulses) between the two unique pace/sense indicators the two message events will not be confused even if any one of the pulses is not detected. For example, an "A" event may be represented as a first pulse 302, followed by a second pulse 304 at T after first pulse 304, followed by a third pulse 306 at 3T after second pulse 304 and 5T after first pulse 302. A "B" event may be represented as a first pulse 310, followed by a second pulse 312 at 2T after first pulse 310, followed by a third pulse 314 at 4T after second pulse 304 and 7T after first pulse 310. Under such a scheme, the receiver can pattern match the A event to a match of either T, 3T or 5T pulse separations and the B event to a match of either 2T, 4T or 7T pulse separations. This concept can be further expanded by adding more transmitted bits and a larger range of spacing to handle multiple bit errors if needed, but there will be additional cost in both transmit and receive currents.

Since such a scheme relies on measuring multiple intervals with a receiver clock that is not synchronized to the transmitter clock the detection must account for clock phase and frequency mismatch between the devices. For example, a transmitted pulse separation of 3T may be measured as 2T if the receiver clock is slightly slower than the transmitted clock, as 3T if they match well, or as 4T if the receiver clock is faster. This can lead to detection errors in pattern matching the two events since the A event can actually be observed as 0T,1T,2T,3T,4T,5T,6T which is not sufficiently different from how the B event would be observed. This may be solved by either sampling with a faster clock (e.g., 2×) or by slowing down and spreading the transmitted pattern by a factor of 2 or more. Since this issue is compounded as longer messages may encounter bit-slip due to frequency mismatch, one solution is to use a more stable crystal oscillator based clock (typically 32 kHz) to time the separation between pulses and the faster microsecond clock to generate the narrow transmission pulses. This does lead to higher receiver current due to a longer message time, but simplifies the bit synchronization without a transmission current penalty.

For example, when additional information is sent that may contain a larger set of possible values, pulse position modulation (PPM) can be employed to minimize the pulses and reduce the power requirement of communication. For example the message could convey a cardiac cycle count with each message so that the receiving device would know if it missed a previous message. In this case, for example, the pulse position may advance with each transmission and then wrap back to the initial position once the last slot is reached. For example, the cycle count modulo 4 could be sent by either 2 binary bit slots or 4 pulse position modulation (PPM) slots. In either case, the average pulse count is 1 pulse. However, if the device also echoes back the last received cycle count, then there would be an average of 2 bits in 4 binary bit locations. With a PPM scheme, only 1 bit would be sent in one of 16 possible locations. Further, another advantage is that single bit error detection is provided.

While the methods and systems described herein include examples primarily in the context of LPs, it is understood that the methods and systems herein may be utilized with various other external and implanted devices. By way of example, the methods and systems may coordinate operation between various implantable medical devices (IMDs) implanted in a human, not just LPs. The methods and systems comprise configuring a first IMD to receive communications from a second IMD through conductive communication over first and second channels. The method and systems maintain the first channel active for at least a portion of a time when the second channel is inactive to listen for event messages from the second IMD. The methods and systems detect an incoming signal at the first IMD over the first channel. The methods and systems determine whether the incoming signal received over the first channel corresponds to a wakeup notice and, when the incoming signal corresponds to the wakeup notice, the methods and systems activate the second channel at the first IMD. The methods and systems include receiving an event message over the second channel from the second IMD. The IMD may represent an LP, an ICD, an S-ICD, a neurostimulation device, or any other implanted medical device.

As described above, in some embodiments, the method further includes transmitting the LP wakeup notice over the first channel from the remote LP and thereafter transmitting the event message over the second channel from the remote LP. Optionally, the event message includes an event marker identifying at least one of a paced and a sensed event that occurred in the chamber where the remote LP is located.

Referring back to FIG. 2, LP 102, 104 includes at least two leadless electrodes 108 configured for delivering cardiac pacing pulses, sensing evoked and/or natural cardiac electrical signals, and unidirectional or bi-directional communication.

LP 102, 104 includes a transmitter 118 and first and second receivers 120 and 122 that collectively define separate first and second communications channels 105 and 107 (FIG. 1) to convey LP trigger pulse(s) and event messaging, respectively, (among other things) between LPs 102 and 104. Optionally, LP 102, 104 communicates conductively over a common physical channel via the same electrodes 108 that are also used to deliver pacing pulses. Usage of the electrodes 108 for communication enables the one or more leadless cardiac pacemakers 102 and 104 for antenna-less and telemetry coil-less communication.

When LP 102, 104 senses an intrinsic event or delivers a paced event, the corresponding LP 102, 104 transmits n LP trigger pulse(s) and implant event message to the other LP 102, 104. For example, when an atrial LP 102 senses/paces an atrial event, the atrial LP 102 transmits an implant event message including an event marker indicative of a nature of the event (e.g., intrinsic/sensed atrial event, paced atrial event). When a ventricular LP 104 senses/paces a ventricular event, the ventricular LP 104 transmits an implant event message including an event marker indicative of a nature of the event (e.g., intrinsic/sensed ventricular event, paced ventricular event). The implant event messages may be formatted in various manners. As one example, as described above, each event message may include a leading trigger pulse (also referred to as an LP receiver wakeup notice) followed by an event marker and/or other information. The notice trigger pulse is transmitted over a first channel (e.g., within a frequency range of 500 Hz to 25 kHz). The notice trigger pulse indicates that an event marker is about to be transmitted over a second channel (e.g., within a higher frequency range with pulses narrower than 10 µs). The event marker is then transmitted over the second channel. The event marker includes data indicative of one or more events (e.g., a sensed intrinsic atrial activation for an atrial located LP, a sensed intrinsic ventricular activation for a ventricular located LP). The event markers include different markers for intrinsic and paced events. The event markers may also indicate start or end times for timers (e.g., an AV interval, a blanking interval, etc.). Optionally, the implant event message may include a message segment that includes additional/secondary information. Such secondary information may include device or sensor status (battery/power cell low, magnet detected, an activity indicator for rate reponse etc).

Optionally, the LP (or IMD) that receives a trigger pulse (s), event message or more generally any i2i communication from another LP (or IMD) or from an external device may transmit a receive acknowledgement indicating that the receiving LP/IMD received the trigger pulse(s), event message, i2i communication, etc.

The event messages enable the LPs 102, 104 to deliver synchronized therapy and additional supportive features (e.g., measurements, etc.). To maintain synchronous therapy, each of the LPs 102 and 104 is made aware (through the event messages) when an event occurs in the chamber containing the other LP 102, 104. Embodiments herein describe efficient and reliable processes to maintain synchronization between LPs 102 and 104 without maintaining constant communication between LPs 102 and 104. In accordance with embodiments herein, the transmitter(s) 118 and receivers 120, 122 utilize low power event messages/ signaling between multiple LPs 102 and 104. The low power event messages/signaling may be maintained between LPs 102 and 104 synchronously or asynchronously.

In some embodiments, for synchronous event signaling, LPs 102 and 104 may maintain synchronization and regularly communicate at a specific interval. Synchronous event signaling allows the transmitter and receivers in each LP 102,104 to use limited (or minimal) power as each LP 102, 104 is only powered for a small fraction of the time in connection with transmission and reception. For example, LP 102, 104 may transmit/receive (Tx/Rx) communications in time slots having duration of 10-20 µs, where the Tx/Rx time slots occur periodically (e.g., every 10-20 ms). In the foregoing example, a receiver 120, 122 that is active/ON for select receive time slots, that are spaced apart several milliseconds, may draw an amount of current that is several times less (e.g., 1000 times less) than a current draw of a receiver that is "always on."

LPs 102 and 104 may lose synchronization, even in a synchronous event signaling scheme. As explained herein, features may be included in LPs 102 and 104 to maintain device synchronization, and when synchronization is lost, LPs 102 and 104 undergo operations to recover synchronization. Also, synchronous event messages/signaling may introduce a delay between transmissions which causes a reaction lag at the receiving LP 102, 104. Accordingly, features may be implemented to account for the reaction lag.

During asynchronous event signaling, LPs 102 and 104 do not maintain communication synchronization. Asynchronous event signaling may be desirable when LPs 102 and 104 are afforded a larger power budget. During asynchronous event signaling, one or more of receivers 120 and 122 of LPs 102 and 104 are "always on" to search for incoming transmissions. However, maintaining LP receivers 120 and 122 in an "always on" state presents challenges as the received signal level often is low due to high channel attenuation caused by the patient's anatomy.

The asynchronous event signaling methods avoid risks associated with losing synchronization between devices. However, the asynchronous event signaling methods utilize additional receiver current between transmissions. For purposes of illustration only, a non-limiting example is described hereafter. For example, the channel may be estimated to have an attenuation factor of $\frac{1}{500}$ to $\frac{1}{10000}$. A gain factor may be $\frac{1}{1000}$th. Transmit current is a design factor in addition to receiver current. To overcome the foregoing receive power limit, a pulsed transmission scheme may be utilized in which communications transmissions occur correlated with an event. By way of example, the pulsed transmission scheme may be simplified such that each transmission constitutes a single pulse of a select amplitude and width.

In accordance with embodiments herein, LPs 102 and 104 utilize multi-stage receivers that implement a staged receiver wakeup scheme in order to improve reliability yet remain power efficient. Each of LPs 102 and 104 includes first and second receivers 120 and 122 that operate with different first and second activation protocols and different first and second receive channels. For example, first receiver 120 has a very low power consumption, e.g., less than 500 nA. First receiver 120 may be assigned a first activation protocol that is "always on" and that listens over a first receive channel that has a lower frequency range (e.g., 500 Hz to 25 kHz) as compared to the frequency range (e.g., greater than 25 KHz) assigned to the second receive channel. First receiver 120 may maintain the first channel active for at least a portion of a time when the second channel is inactive to listen for event messages from a remote LP. The controller or processor determines whether the incoming signal received over the first channel corresponds to an LP wakeup notice. The second receiver 122 may be assigned a second activation protocol that is a triggered protocol, in which the second receiver 122 becomes active in response to detection of trigger events over the first receive channel (e.g., when the incoming signal corresponds to the LP wakeup notice, activating the second channel at the local LP).

The frequency ranges of the first and second receive channels can be set such that a lower power trigger pulse (e.g., an approximately 20-50 μsec pulse) is detectable over the first receive channel as the notice/trigger event by processor 112. In response thereto, processor 112 directs second stage receiver 122 to wake up (e.g., be activated or enabled). Second stage receiver 122 detects and decodes a higher frequency marker message (e.g., from another LP, ICD, or programmer) that follows the notice/trigger event pulse. The marker message may represent a signature indicative of an event qualification to qualify a valid event marker pulse. The event qualification messages distinguish a message from spurious noise and avoid mistaking other signals as event messages having implant markers. The lower level trigger pulse may also include a signature to facilitate distinguishing the lower level trigger pulse from noise. The event message may be repeated to allow the LP receiver 120 multiple chances to 'catch' the event qualification. Additionally or alternatively, the Tx 118 and Rx 120, 122 may implement a handshaking protocol in which the Tx 118 and Rx 120, 122 exchange additional information, such as to allow a response to follow the marker. The exchange of additional information may be limited or avoided in certain instances as the exchange draws additional power when sending and receiving the information. Optionally, the event message may be configured with additional content to provide a more robust event marker. Further, in some embodiments, the low level trigger pulses and high level message pulses may change in polarity to aid detection, and/or may be repeated in back to back pulses to facilitate improving detection.

Transmitters 118 are configured to transmit the event messages in a manner that does not inadvertently capture the heart in the chamber where LP 102 or 104 is located, such as when the associated chamber is not in a refractory state. In addition, LP 102, 104 that receives an event message may enter an 'event refractory' state (or event blanking state) following receipt of the event message. The event refractory/blanking state may be set to extend for a determined period of time after receipt of an event message in order to avoid the receiving LP 102, 104 to inadvertently sense another signal as an event message that might otherwise cause retriggering. For example, the receiving LP 102, 104 may detect a measurement pulse from another LP 102, 104 or programmer 109.

In accordance with embodiments herein, programmer 109 may communicate over a programmer-to-LP channel, with LP 102, 104 utilizing the same event message scheme. The external programmer may listen to the event message transmitted between LP 102, 104 and synchronize programmer to implant communication such that programmer 109 does not transmit and receive communications signals 113 and 111 until after an implant to implant messaging sequence is completed.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

FIG. 2 depicts a single LP 102 and shows the LP's functional elements substantially enclosed in a hermetic housing 110. The LP 102 has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery or power cell 114 to supply power for pacing, sensing, and communication. The housing 110 also contains circuits 132 for sensing cardiac activity from the electrodes 108, circuits 134 for receiving information from at least one other device via the electrodes 108, and a pulse generator 116 for generating pacing pulses for delivery via the electrodes 108 and also for transmitting information to at least one other device via the electrodes 108. The housing 110 can further contain circuits for monitoring device health, for example a battery/power cell current monitor 136 and a battery/power cell voltage monitor 138, and can contain circuits for controlling operations in a predetermined manner.

Additionally or alternatively, one or more leadless electrodes 108 can be configured to communicate bi-directionally among the multiple leadless cardiac pacemakers and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bi-directionally among the one or more leadless cardiac pacemakers 102 and/or the ICD 106 and transmit data including designated codes for events detected or created by an individual pacemaker. Individual pacemakers can be configured to issue a unique code corresponding to an event type and a location of the sending pacemaker.

Information communicated on the incoming communication channel can include but is not limited to pacing rate, pulse duration, sensing threshold, and other parameters commonly programmed externally in conventional pacemakers. Information communicated on the outgoing communication channel can include but is not limited to programmable parameter settings, pacing and sensing event counts, battery/power cell voltage, battery/power cell current, device health, and other information commonly displayed by external programmers used with conventional pacemakers. The outgoing communication channel can also echo information from the incoming channel, to confirm correct programming.

For example, in some embodiments an individual LP 102 can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 104 may receive and relay an event message from LP 102 to the programmer. Similarly, information communicated on the outgoing channel can also include a message to another leadless cardiac pacemaker or pacemakers, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an implantable cardioverter-defibrillator (ICD) 106 in addition to the leadless cardiac pacemakers 102, 104 configured for implantation in electrical contact with a cardiac chamber and for performing cardiac rhythm management functions in combination with the implantable ICD 106. The implantable ICD 106 and the one or more leadless cardiac pacemakers 102 configured for leadless intercommunication by information conduction through body tissue and/or wireless transmission between transmitters and receivers in accordance with the discussed herein.

In a further embodiment, a cardiac pacing system 100 comprises at least one leadless cardiac pacemaker 102 configured for implantation in electrical contact with a cardiac chamber 104 and configured to perform cardiac pacing functions in combination with the co-implanted implantable cardioverter-defibrillator (ICD) 106. The leadless cardiac pacemaker or pacemakers 102 comprise at least two leadless electrodes 108 configured for delivering cardiac pacing pulses, sensing evoked and/or natural cardiac electrical signals, and transmitting information to the co-implanted ICD 106.

As shown in the illustrative embodiments, a leadless cardiac pacemaker 102 can comprise two or more leadless electrodes 108 configured for delivering cardiac pacing pulses, sensing evoked and/or natural cardiac electrical signals, and bi-directionally communicating with the co-implanted ICD 106. A leadless cardiac pacemaker 102 can be configured to communicate with other pacemakers and/or communicate with a non-implanted programmer via communication that has communication power requirements essentially met by power consumed in cardiac pacing. For example, the leadless cardiac pacemaker 102 can be configured to communicate with other pacemakers and with a non-implanted programmer via communication that has negligible transmission power requirements in addition to power consumed in cardiac pacing.

LP 102, 104 can be configured for operation in a particular location and a particular functionality at manufacture and/or at programming by an external programmer. Bidirectional communication among the multiple leadless cardiac pacemakers can be arranged to communicate notification of a sensed heartbeat or delivered pacing pulse event and encoding type and location of the event to another implanted pacemaker or pacemakers. LP 102, 104 receiving the communication decode the information and respond depending on location of the receiving pacemaker and predetermined system functionality.

Also shown in FIG. 2, the primary battery/power cell 114 has positive terminal 140 and negative terminal 142. In certain embodiments, battery/power cell 114 is a lithium carbon monofluoride (Li/CFx) battery/power cell. A suitable primary battery/power cell has a volume less than 1 cubic centimeter, and a lifetime greater than 5 years, assuming therapy that utilizes 2.5V amplitude, 0.4 ms pulses at 100% pacing. The current disclosure permits communication using less than approximately 30-50% of the overall budget of the battery/power cell. Current from the positive terminal 140 of primary battery/power cell 114 flows through a shunt 144 to a regulator circuit 146 to create a positive voltage supply 148 suitable for powering the remaining circuitry of the pacemaker 102. The shunt 144 enables the battery/power cell current monitor 136 to provide the processor 112 with an indication of battery/power cell current drain and indirectly of device health. The illustrative power supply can be a primary battery/power cell 114. In some embodiments, the power supply can be selected as a primary battery/power cell 114 that has a volume less than approximately 1 cubic centimeter.

In various embodiments, LP 102, 104 can manage power consumption to draw limited power from the battery/power cell, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery/power cell.

Figure 5:
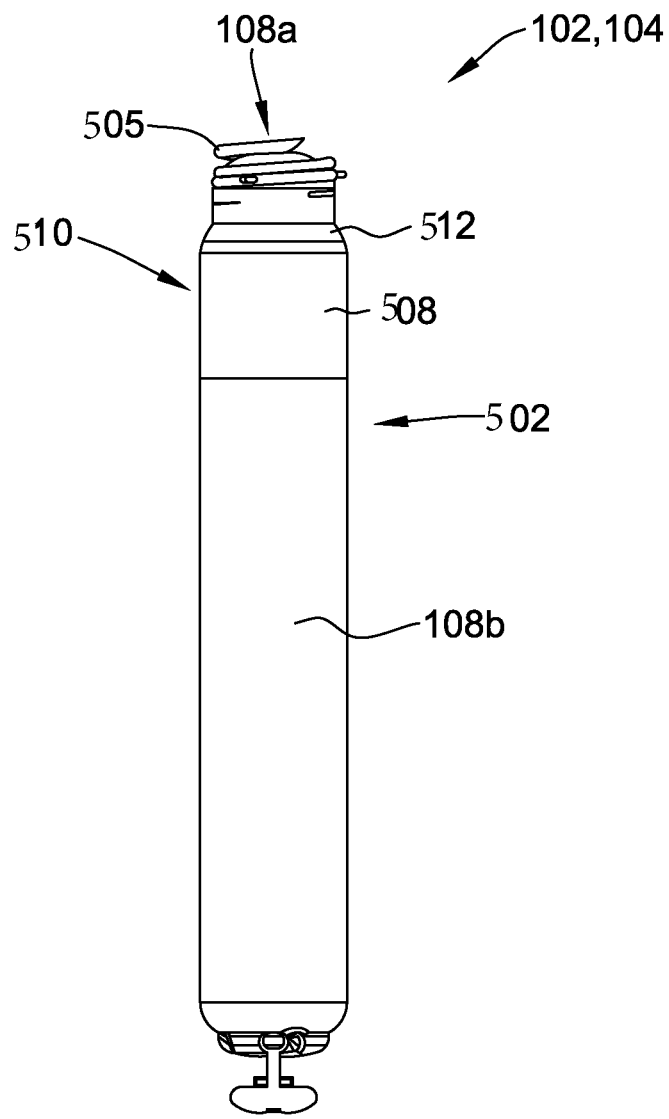
FIG. 5 illustrates a LP in accordance with embodiments herein.

FIG. 5 illustrates a LP 102, 104. The LP can include a hermetic housing 502 with electrodes 108*a* and 108*b* disposed thereon. As shown, electrode 108*a* can be separated from but surrounded partially by a fixation mechanism 505, and the electrode 108*b* can be disposed on the housing 502. The fixation mechanism 505 can be a fixation helix, a plurality of hooks, barbs, or other attaching features configured to attach the pacemaker to tissue, such as heart tissue.

The housing can also include an electronics compartment 510 within the housing that contains the electronic components necessary for operation of the pacemaker, including, for example, a pulse generator, communication electronics, a battery, and a processor for operation. The hermetic housing 502 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108$a$ and 108$b$. The insulator can be an insulative coating on a portion of the housing between the electrodes, and can comprise materials such as silicone, polyurethane, parylene, or another biocompatible electrical insulator commonly used for implantable medical devices. In the embodiment of FIG. 5, a single insulator 508 is disposed along the portion of the housing between electrodes 108$a$ and 108$b$. In some embodiments, the housing itself can comprise an insulator instead of a conductor, such as an alumina ceramic or other similar materials, and the electrodes can be disposed upon the housing.

As shown in FIG. 5, the pacemaker can further include a header assembly 512 to isolate 108$a$ and 108$b$. The header assembly 512 can be made from PEEK, tecothane or another biocompatible plastic, and can contain a ceramic to metal feedthrough, a glass to metal feedthrough, or other appropriate feedthrough insulator as known in the art.

The electrodes 108$a$ and 108$b$ can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 5, electrode 108$a$ can be a pace/sense electrode and electrode 108$b$ can be a return electrode. The electrode 108$b$ can be a portion of the conductive housing 502 that does not include an insulator 508.

Several techniques and structures can be used for attaching the housing 502 to the interior or exterior wall of the heart. A helical fixation mechanism 505, can enable insertion of the device endocardially or epicardially through a guiding catheter. A torqueable catheter can be used to rotate the housing and force the fixation device into heart tissue, thus affixing the fixation device (and also the electrode 108$a$ in FIG. 5) into contact with stimulable tissue. Electrode 108$b$ can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads. The distance between electrodes 108A and 108B may be, for example, approximately 25 millimeters (mm).

There are tradeoffs in selecting this distance. On the one hand, the larger the electrode separation is, the larger the channel gain is (i.e., the channel gain is approximately proportional to the product of electrode separations at the transmitter and receiver, although there are corrections due to current spread over the uncoated, conductive surface of the can electrode). The larger the channel gain is, the less transmitted power is required for communication. On the other hand, the smaller the electrode separation is, the more targeted/selective are pacing and sensing processes (because, in this embodiment, the same electrodes used for pacing and sensing are used for communication). Therefore, the optimal range of electrode separation may be relatively broad, for example between 10 mm and 30 mm.

The module/controller may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the (module/controller) represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The (module/controller) may execute a set of instructions that are stored in one or more storage elements, in order to process data. The storage elements may also store data or other information as desired or needed. The storage element may be in the form of an information source or a physical memory element within the (module/controller). The set of instructions may include various commands that instruct the (module/controller) to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

Figure 6:
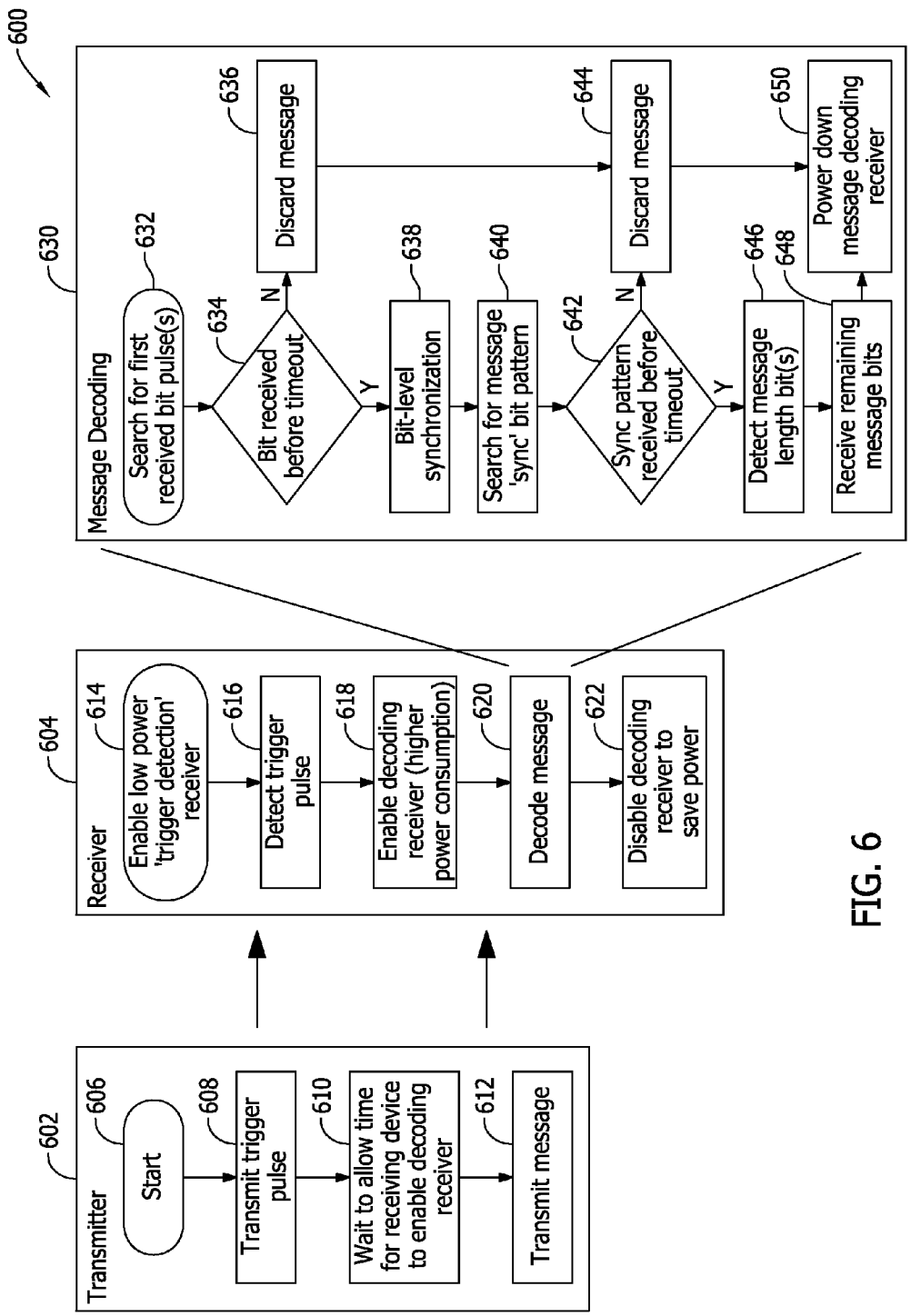
FIG. 6 is a diagram showing one embodiment of method for communicating between a transmitter and a receiver during an i2i message operation according to one embodiment.

FIG. 6 is a diagram showing one embodiment of method 600 for communicating between a transmitter device 602 and a receiver device 604 during an i2i message operation. Transmitter device 602 may be, for example, one of LPs 102 and 104, and receiver device 604 may be the other of LPs 102 and 104. Method 600 initializes at block 606 when an event (e.g., a pace event or sense event) occurs. At block 608, in response to the event, transmitter device 602 transmits a trigger pulse (e.g., trigger pulse 202 (shown in FIG. 3)) to receiver device 604. After block 608, transmitter device 602 waits a predetermined period of time (e.g., $T_2$ (shown in FIG. 3)) at block 610 to allow time for receiver device 604 to activate in response to the trigger pulse. After the predetermined period of time, at block 612, transmitter device 602 transmits a message pulse (e.g., message content pulse 204 (shown in FIG. 3)) to receiver device 604.

At block 614 (which generally occurs temporally prior to block 606), receiver device 604 enables a low power trigger detection receiver to detect any received trigger pulses. At block 616, receiver device 604 detects the trigger pulse transmitted at block 608. In response, receiver device 604 enables a higher power consumption decoding receiver that is able to detect any received message pulses at block 618. At block 620, receiver device 604 receives and decodes the message pulse transmitted at block 612 to identify the event. Then, to save power, receiver device 604 deactivates the higher power consumption decoding receiver at block 622.

FIG. 6 also illustrates one embodiment of a message decoding scheme 630. As shown in FIG. 6, block 620 may be implemented using message decoding scheme 630.

In message decoding scheme, at block 632, receiver device 604 searches for the first received bit pulse in the message pulse for a first predetermined period of time. At block 634, if the bit is not received within the first predetermined period of time, flow proceeds to block 636, and the received message is discarded. If the bit is received within the first predetermined period of time, flow proceeds to block 638.

At block 638, bit-level synchronization is initiated, and at block 640, receiver device 604 searches for a synchronization pattern in the message for a second predetermined period of time. In this embodiment, multiple valid synchronization pattern(s) may be used to capture the timing and the most essential information (i.e., pace vs sense) in the same pattern. At block 642, if the synchronization pattern is not received within the second predetermined period of time, flow proceeds to block 644, and the received message is discarded. If the synchronization pattern is received within the second predetermined period of time, flow proceeds to block 646, where receiver device 604 checks for a bit pattern that indicates the remaining message length to decode. At block 648, any remaining message bits are received, and at block 650, receiver device 604 initiates deactivation of the higher power consumption decoding receiver functionality. Blocks 636 and 644 also flow to block 650.

Although the low powered 'trigger detection' receiver may be continuously on in some embodiments, there may be cases where no messages are expected for a time and the low powered 'trigger detection' receiver can also be temporarily powered off to save further current. Such a case may be, for example, during the refractory period after a valid received event occurs.

Embodiments of the present disclosure use novel multi-stage detection receivers, multiple frequency pulses and minimal transmit pulse widths, syncword event markers, error detection schemes, and number of pulses to communicate on every cardiac cycle. This allows event signaling to occur between the LP devices so that they can synchronize delivered therapy and also status and command message passing to occur.

The present disclosure advantageously provides for the use of smaller implant power sources and therefore smaller device size and/or increased device longevity when compared with other implant communication schemes. It does so without using additional components or physical structures as compared to inductive or RF based schemes. It also does so with low peak current requirements which would impose additional restrictions on the power source.

The present disclosure advantageously provides for sufficient range of communication under severe constraints on peak/average transmitted power and transmitter/receiver size by using conductive communication between essentially current dipoles.

The transmitting dipole current source pushes the transmitted current through somewhat conductive surrounding medium, a process that results in electric field covering the communication range. The electric field local to the receiver region field is picked up by the receiving dipole, filtered, amplified, and further conditioned. Unlike communication based on RF, inductive, or capacitive coupling, the communication channel gain is intrinsically almost independent of the transmission frequency. That independence allows us to combine both small device size with relatively low transmission frequency, hence with low power budget.

Furthermore, communication based on RF, inductive, or capacitive coupling actually suffers from nonzero medium conductivity, because such conductivity reduces channel gain. On the other hand, conductive communication benefits from some medium conductivity, because conductive medium enables lower communication frequencies, as well as lower source impedance at the receiver.

Given that Tx-Rx separation is comparable with or larger than the effective size of the communication dipoles (the latter being limited from above by the device sizes), the channel gain is approximately the same as for dipole-dipole interaction (with relatively minor contributions from higher multipoles).

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A method for coordinating synchronized operation between two or more implantable medical devices (IMDs), the method comprising:
    configuring a first IMD to receive communications from a second IMD through conductive communication over first and second channels;
    maintaining the first channel active for at least a portion of a time when the second channel is inactive to listen for event messages from the second IMD;
    detecting an incoming signal at the first IMD over the first channel;
    determining whether the incoming signal received over the first channel corresponds to a message trigger pattern;
    when the incoming signal corresponds to the message trigger pattern, activating the second channel at the second IMD; and receiving an event message over the second channel from the first IMD using a first receiver of the second IMD.

2. The method of claim 1, wherein detecting an incoming signal comprises using a first receiver of the second IMD to detect the incoming signal, and wherein receiving an event message comprises using a second receiver of the second IMD to receive the event message.

3. The method of claim 1, wherein the first and second channels have different first and second pulse durations, wherein the first pulse duration is wider than the second pulse duration, so as to lower the current consumption of the first receiver of the second IMD.

4. The method of claim 1, further comprising:
transmitting the message trigger pattern from the first IMD over the first channel; and
transmitting the event message from the first IMD over the second channel.

5. The method of claim 1, wherein the first and second IMDs are cardiac pacemakers, and wherein the event message includes an event marker identifying at least one of a paced and a sensed event in the chamber where the second IMD is located.

6. The method of claim 1, wherein transmit power of the first IMD is reduced by using transmit amplitudes equal to or less than approximately an energy cell voltage level of the first IMD.

7. The method of claim 1, wherein transmit power of the first IMD is reduced by using transmit amplitudes equal to or less than approximately three times an energy cell voltage level of the first IMD.

8. The method of claim 3, wherein the pulses do not include a carrier in order to reduce transmit power of the first IMD.

9. The method of claim 3, wherein event messages are encoded by pulse separation or spacing to reduce pulse count and transmit power of the first IMD.

10. The method of claim 1, wherein the first receiver of the second IMD is always on in order to detect messages at any time.

11. The method of claim 1, wherein the first and second channels have different first and second pulse durations, wherein the second pulse duration is narrower than the first pulse duration, so as to reduce the transmit current consumption of the second channel of the first IMD.

12. The method of claim 1, wherein highest priority information is encoded within unique synchronization patterns of the event message.

13. The method of claim 1, wherein message error protection is provided in the event message by selection of unique pulse separation or spacing patterns.

14. A system for coordinating synchronized operation between two or more implantable medical devices (IMDs), the system comprising at least a first IMD and a second IMD comprising a first receiver, wherein the first IMD is configured to:
receive communications from the second IMD through conductive communication over first and second channels;
maintain the first channel active for at least a portion of a time when the second channel is inactive to listen for event messages from the second IMD;
detect an incoming signal over the first channel; and
determine whether the incoming signal received over the first channel corresponds to a message trigger pattern, and wherein the second IMD is configured to:
activate the second channel, when the incoming signal corresponds to the message trigger pattern; and
receive an event message over the second channel from the first IMD using the first receiver of the second IMD.

15. The system of claim 14, the second IMD further comprising a second receiver and wherein the second IMD is further configured to:
detect an incoming signal using the first receiver to detect the incoming signal, and
receive an event message using the second receiver of the second IMD.

16. The system of claim 14, wherein the first and second channels have different first and second pulse durations, wherein the first pulse duration is wider than the second pulse duration.

17. The system of claim 14, wherein the first IMD is further configured to:
transmit the message trigger pattern over the first channel; and
transmitting the event message over the second channel.

18. The system of claim 14, wherein the first and second IMDs are cardiac pacemakers, and wherein the event message includes an event marker identifying at least one of a paced and a sensed event in the chamber where the second IMD is located.

19. The system of claim 14, wherein the first IMD is configured to use transmit amplitudes equal to or less than approximately an energy cell voltage level of the first IMD.

20. The system of claim 14, wherein the first IMD is configured to use transmit amplitudes equal to or less than approximately three times an energy cell voltage level of the first IMD.

21. The system of claim 14, wherein the pulses do not include a carrier in order to reduce transmit power of the first IMD.

22. The system of claim 14, the first IMD is configured to encode event messages by pulse separation or spacing.

23. The system of claim 14, wherein the first receiver of the second IMD is configured to be always on in order to detect messages at any time.

24. The system of claim 14, wherein the first IMD is configured to encode highest priority information within unique synchronization patterns of the event message.

25. The system of claim 14, wherein the first IMD is configured to provide message error protection in the event message by selection of unique pulse separation or spacing patterns.

* * * * *